United States Patent
Mitterer et al.

(10) Patent No.: US 10,202,417 B2
(45) Date of Patent: *Feb. 12, 2019

(54) PURIFICATION METHOD FOR VITAMIN K DEPENDENT PROTEINS BY ANION EXCHANGE CHROMATOGRAPHY

(71) Applicants: Baxalta Incorporated, Bannockburn, IL (US); Baxalta GmbH, Zug (CH)

(72) Inventors: Artur Mitterer, Orth/Donau (AT); Meinhard Hasslacher, Vienna (AT); Christian Fiedler, Vienna (AT); Dominik Mittergradnegger, Vienna (AT)

(73) Assignees: Baxalta Incorporated, Bannockburn, IL (US); Bazalta GmbH, Zug (CH)

( * ) Notice: Subject to any disclaimer, the term of this patent is extended or adjusted under 35 U.S.C. 154(b) by 55 days.

This patent is subject to a terminal disclaimer.

(21) Appl. No.: 14/776,622

(22) PCT Filed: Mar. 14, 2014

(86) PCT No.: PCT/EP2014/055120
§ 371 (c)(1),
(2) Date: Sep. 14, 2015

(87) PCT Pub. No.: WO2014/140289
PCT Pub. Date: Sep. 18, 2014

(65) Prior Publication Data
US 2016/0039869 A1    Feb. 11, 2016

Related U.S. Application Data

(60) Provisional application No. 61/792,772, filed on Mar. 15, 2013.

(51) Int. Cl.
*C07K 1/18* (2006.01)
*C12N 9/64* (2006.01)
*C07K 14/745* (2006.01)

(52) U.S. Cl.
CPC .............. *C07K 1/18* (2013.01); *C07K 14/745* (2013.01); *C12N 9/644* (2013.01); *C12Y 304/21022* (2013.01)

(58) Field of Classification Search
None
See application file for complete search history.

(56) References Cited

U.S. PATENT DOCUMENTS 4,981,952 A    1/1991  Yan
5,633,350 A *  5/1997  Fischer ................ C07K 14/745
                                                    530/380
6,869,934 B2   3/2005  Mizokami
2008/0207879 A1* 8/2008 Artur ....................... C07K 1/18
                                                    530/384
2009/0311239 A1  12/2009 Chtourou et al.
2010/0047428 A1  2/2010  Lejars et al.

FOREIGN PATENT DOCUMENTS

| EP | 0 363 126 A2 | 4/1990 |
| WO | WO 94/05692 A1 | 3/1994 |
| WO | WO 96/40883 A1 | 12/1996 |
| WO | WO 98/35689 A1 | 8/1998 |
| WO | WO 2006/035058 A2 | 4/2006 |
| WO | WO 2006/067230 A1 | 6/2006 |
| WO | WO 2007/026020 A1 | 3/2007 |
| WO | WO 2011/073235 A1 | 6/2011 |
| WO | WO 2011/135071 A1 | 11/2011 |
| WO | WO 2013/053887 A1 | 4/2013 |
| WO | WO 2013/053888 A1 | 4/2013 |

OTHER PUBLICATIONS

Kelley et al. Validation of Biopharmaceutical Manufacturing Processes ACS Symposium Series vol. 698 chapter 8: 93-113 (1998).*
International Search Report dated May 16, 2014, for International Patent Application No. PCT/EP2014/055120,4 pages.
U.S. Appl. No. 14/351,541, filed Oct. 17, 2014.
U.S. Appl. No. 15/615,696, filed Jun. 6, 2017.
U.S. Appl. No. 13/098,313, filed Apr. 29, 2011.
Burger, A. et al., "A rapid and efficient purification method for recombinant annexin V for biophysical studies," FEBS, Aug. 1993, vol. 329, No. 1, 2, pp. 25-28.
Harrison, S. et al., "The Manufacturing Process for Recombinant Factor IX," *Seminars in Hematology*, Apr. 1998, vol. 35, No. 2, Suppl 2, pp. 4-10.
Josic, D. et al., "Preparation of vitamin K-dependent proteins, such as clotting factors II, VII, IX and X and clotting inhibitor Protein C," *Journal of Chromatography B*, 2003, vol. 790, pp. 183-197.
Kelley, B.D. et al., "Robustness Testing of a Chromatographic Purification Step Used in Recombinant Factor IX Manufacture," Chapter 8 in *Validation of Biopharmaceutical Manufacturing Processes, American Chemical Society*, 1998, pp. 93-113.
Osborn, E.C., "The Employment of Deae-Cellulose Columns on a 'Rejection' Principle in the Preparation of Factor VII," Clinica Chimica Acta, 1965, vol. 12, pp. 415-418.

* cited by examiner

*Primary Examiner* — Christian L Fronda
(74) *Attorney, Agent, or Firm* — Morgan, Lewis & Bockius, LLP

(57) ABSTRACT

The present invention relates to a method for the purification of Vitamin K dependent proteins with high yield and high purity, particularly enriched in active protein, on anion exchange resin materials, to Vitamin K dependent proteins obtainable by said method, and to a kit comprising means for carrying out said method.

9 Claims, 3 Drawing Sheets

Figure 1:
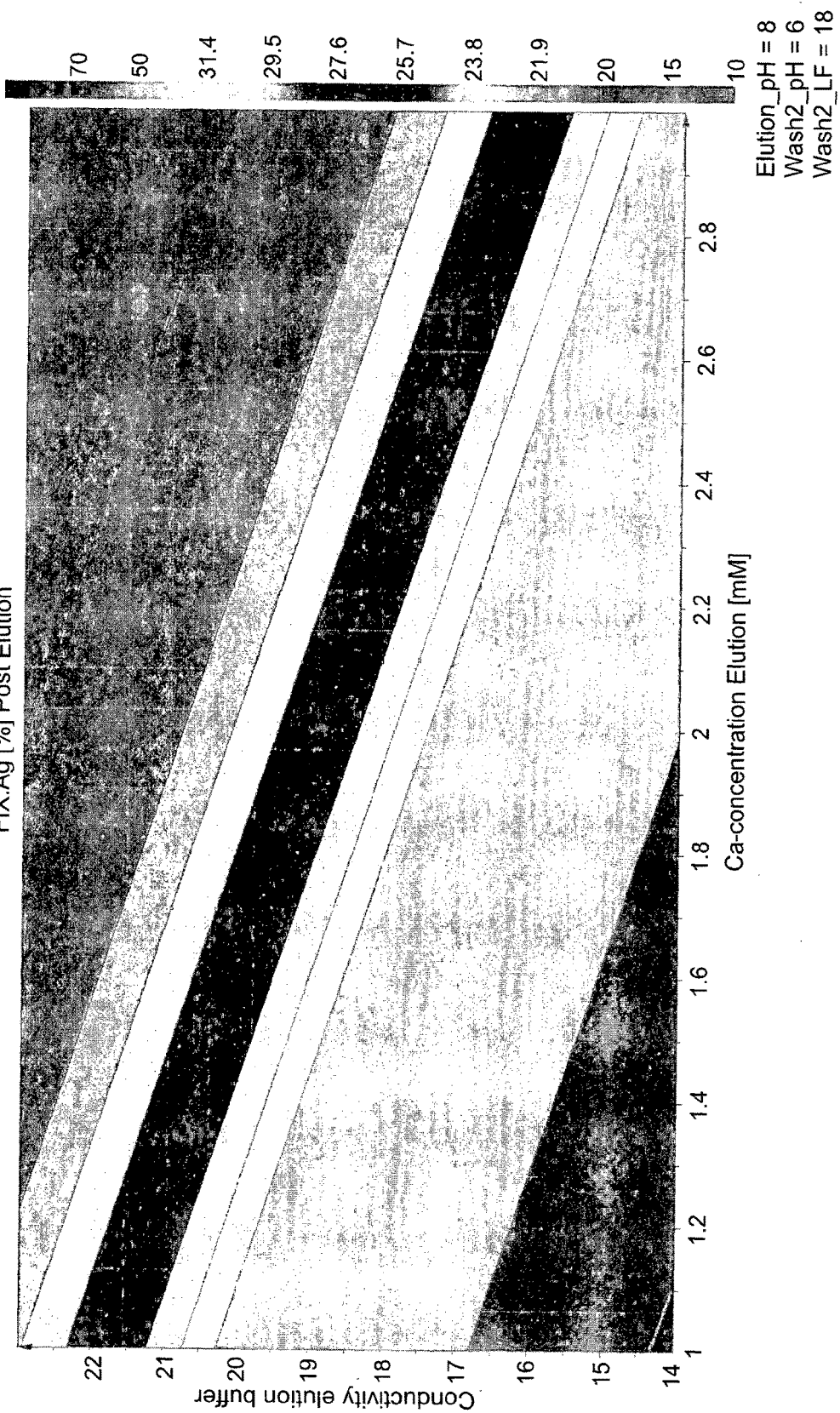

PURIFICATION METHOD FOR VITAMIN K DEPENDENT PROTEINS BY ANION EXCHANGE CHROMATOGRAPHY

CROSS-REFERENCE TO RELATED APPLICATIONS

This application is a U.S. National Phase of International Application No. PCT/EP2014/055120, filed Mar. 14, 2014, which claims the benefit of U.S. Provisional Application No. 61/792,772, filed Mar. 15, 2013, the disclosures of which are hereby incorporated herein by reference in their entirety for all purposes.

FIELD OF THE INVENTION

The present invention relates to a method for the purification of Vitamin K dependent proteins, in particular (recombinant) FIX, with high yield and high purity on anion exchange resin materials, to Vitamin K dependent proteins, in particular FIX, preferably obtainable by said method, and to a kit comprising means for carrying out said method.

BACKGROUND OF THE INVENTION

Since the advent of recombinant technology, many mammalian proteins are produced in host cells by e.g. transfecting cells with DNA encoding said proteins and growing the recombinant cells under conditions favorable for the expression of said proteins. The proteins secreted by the cells into the cell culture medium, or residing inside the cells, can be separated from the culture medium and other components using chromatographic techniques, e.g. ion exchange chromatography, affinity chromatography, and the like. For further pharmaceutical applications, purity is of particular importance. However, at the same time the biological activity of the protein must be preserved after thorough purification of the proteins of interest. The concept of eluting Calcium binding proteins from anion exchange resins by divalent cations was firstly reported almost thirty years ago. Although bovine Factor VII was successfully isolated from bovine plasma, the purification of human Factor VII was still problematic, i.e. the material produced was only partially pure or was obtained in very small quantities. Workers in the field succeeded in the isolation of human Factor VII from human plasma in sufficient quantities (with a yield of approx. 30%) by means of adsorbing proteins to a divalent cation, i.e. barium citrate, and then separating the protein by anion exchange chromatography. Further, methods were available for recovering and purifying vitamin K-dependent proteins from the medium of a cell culture producing vitamin K-dependent proteins with different specific activities by means of conventional ion-exchange resins, e.g. anion exchange resins, and using an eluant containing divalent cations, e.g. calcium ion ($Ca^{2+}$), magnesium ion ($Mg^{2+}$), barium ion ($Ba^{2+}$), and strontium ion ($Sr^{2+}$).

Furthermore, methods were available for the purification of Factor IX (FIX) in solution, comprising the steps of applying the solution containing FIX to an anion exchange resin, washing the anion exchange resin with a solution having a conductivity that is less than required to elute FIX from the resin, and eluting FIX from the anion exchange resin with a first eluant including divalent cations to form a first eluate. The first eluate is then applied to a heparin or heparin-like resin to form a second eluate, and the second eluate is applied to hydroxyapatite to form a third eluate, utilizing a high conductivity washing agent in the washing step.

Factor IX (FIX) is a vitamin K-dependent serine protease of the coagulation system, belonging to the peptidase family S1. FIX is inactive unless activated by Factor XIa or Factor VIIa. For its activation, calcium, and membrane phospholipids, are required. Deficiency of FIX causes the hereditary recessive bleeding disorder hemophilia B, which can be successfully treated by administration of posttranslational modified, i.e. phosphorylated and sulfated FIX. FIX can be further converted into "activated" (further processed) FIX, i.e. FIXa. As FIXa can negatively affect a given composition of FIX (e.g. by increasing its thrombogenicity as described in the literature), FIX products should preferentially contain a low FIXa content. Care needs to be taken to not confuse "activated" FIX, i.e. FIXa, which is a further processed FIX having the above described possibly negative effects, with active FIX which is the FIX which has a desired activity in a given subject and has not yet been further processed e.g. by FXIa or FVIIa. It is thus equally important that a FIX product has a high content of active FIX, and a low content of inactive FIX, preferably together with a low content of "activated" FIXa. Possible inactive FIX can be FIX with a pro-peptide, FIX with a low gamma-carboxylation, oxidized FIX, de-amidated FIX, FIX with an incorrect tertiary structure etc. Further, Factor VII (FVII) is a vitamin K-dependent serine protease which plays a significant role in the coagulation cascade, where it initiates the process of coagulation with tissue factor (TF). Upon vessel injury, TF is exposed to the blood and circulating FVII. Once bound to TF, FVII is activated to FVIIa by thrombin, Factor Xa, IXa, XIIa, and the FVIIa-TF complex whose substrates are FX and FIX.

Thus, the problem underlying the present invention is to provide an improved method for the purification of vitamin K-dependent proteins with high yield and high purity, preferably with a low content of inactive FIX. The solution to the above technical problem is achieved by the embodiments characterized in the claims.

SUMMARY OF THE INVENTION

The present invention—in a preferred embodiment (item 1))—relates to a method for the purification of a Vitamin K-dependent protein comprising the steps of:
 (a) loading an anion exchange resin material (in the following also "the first anion exchange resin material") with the Vitamin K dependent protein in a loading buffer in the absence or low concentration of divalent cations, optionally followed by one to three wash steps;
 (b) eluting the Vitamin K dependent protein with an eluant comprising calcium and a counter-anion to form an eluate containing the Vitamin K dependent protein, wherein:
  1-3 mM calcium is comprised in the eluant
  the eluant has a conductivity of 14-23 mS/cm (25° C.), and
  the pH of the eluant is between 7.0 and 9.0.

In that regard, step (a) as described above is preferably carried out the absence of free divalent cations. "Free" divalent cations in that context shall mean non-complexed divalent cations. That is, if e.g. approximately 1 mM $Ca^{++}$ was present complexed to EDTA, that would still be considered to be in the absence of (free) divalent cations.

In a further preferred embodiment, the method for purification further comprises the following steps:

(c) diluting the obtained eluate pool, ((1) to optionally lower the conductivity), and increasing the concentration of the calcium,
(d) loading a second anion exchange resin material with the eluate as obtained after step (c); and
(e) collecting the flow-through containing the Vitamin K dependent protein.

The optional step c(1) of lowering the conductivity is necessary only, if the conductivity has not already been lowered in the last optional wash step; preferably, the lowering of the conductivity is carried out in wash step 3, as described in more detail below.

The following describes preferred combinations for the parameters shown as being decisive for the separation of inactive vitamin K-dependent protein. All inventive parameter ranges described herein refer to the elution step (b).

The method according to item 1, wherein in step (b):
The conductivity is between 18 and 20 mS/cm (25° C.) at a pH of 7.0-7.4 and 1 mM $Ca^{++}$
the conductivity is between 18.5 and 21 mS/cm (25° C.) at a pH of 7.4-7.6 and 1 mM $Ca^{++}$
the conductivity is between 19 and 22.5 mS/cm (25° C.) at a pH of 7.6-8.0 and 1 mM $Ca^{++}$
the conductivity is between 20 and 23 mS/cm (25° C.) at a pH of 8.0-9.0 and 1 mM $Ca^{++}$
the conductivity is between 15 and 17.0 mS/cm (25° C.) at a pH of 7.0-7.4 and 2 mM $Ca^{++}$
the conductivity is between 16 and 18 mS/cm (25° C.) at a pH of 7.4-7.6 and 2 mM $Ca^{++}$
the conductivity is between 16.5 and 19.5 mS/cm (25° C.) at a pH of 7.6-8.0 and 2 mM $Ca^{++}$
the conductivity is between 17.5 and 21 mS/cm (25° C.) at a pH of 7.6-8.0 and 2 mM $Ca^{++}$
the conductivity is between 19.5 and 22 mS/cm (25° C.) at a pH of 8.0-9.0 and 2 mM $Ca^{++}$
the conductivity is between 14.0 and 15 mS/cm (25° C.) at a pH of 7.0-7.4 and 3 mM $Ca^{++}$
the conductivity is between 15 and 15.5 mS/cm (25° C.) at a pH of 7.4-7.6 and 3 mM $Ca^{++}$
the conductivity is between 14 and 16.5 mS/cm (25° C.) at a pH of 7.6-8.0 and 3 mM $Ca^{++}$, or
the conductivity is between 15 and 19 mS/cm (25° C.) at a pH of 8.0-9.0 and 3 mM $Ca^{++}$.

In a particularly preferred embodiment of the elution (b), the range for conductivity and pH are chosen from the hatched areas in FIG. 2A for a concentration of 1 mM $Ca^{++}$, while they are chosen from the hatched areas in FIG. 2B for a concentration of 2 mM $Ca^{++}$, and while they are chosen from the hatched areas in FIG. 2C for a concentration of 3 mM $Ca^{++}$.

In a further preferred embodiment of the elution (b), the conductivity and concentration of $Ca^{++}$ are chosen
for a pH of 7.0 on the basis of the hatched areas of FIG. 3A
for a pH of 8.0 on the basis of the hatched areas of FIG. 3B, and
for a pH of 9.0 on the basis for the hatched areas of FIG. 3C.

All parameters of calcium concentration, pH and conductivity of the eluant (i.e. the elution buffer) as described above are important parameters. All can interfere with the elution that takes place on the anion exchange resin and influence the final purity of the desired protein.

Very surprisingly, the inventors also could show that a lower concentration of $Ca^{++}$ was necessary than previously thought in the prior art to achieve an advantageous result.

The present inventors have surprisingly found that these parameters need to be controlled in more narrow ranges than previously thought and in particular in a specific relationship to each other, if an inactive target protein shall be separated from an active target protein. The inventors have shown that e.g. inactive rFIX can be separated from active rFIX by keeping the above parameters controlled as described herein. In particular, the inactive FIX could be separated efficiently in the presently described purification scheme. Very surprisingly, the inventors could also show that a pH shift from load/wash to elution on the first anion exchange material was not necessary, as long as the parameter ranges were fixed as described above or as shown in the hatched areas of the enclosed figures.

"active FIX" is FIX which has the desired activity in a given subject. The inventors believe, although this is a hypothesis only and they should not be bound thereto, that the active FIX is a full length single chain molecule without pro-FIX carrying gamma carboxylations at the N-terminus and having full structural integrity (correct disulfide bonding, secondary and tertiary structure) as well as glycosylation. "Inactive FIX" is a FIX which does not have the desired activity in a given subject. According to one possible theory, inactive FIX can origin from under-carboxylation, pro-peptide content, oxidation, deamidation, structural disintegration, disulfide bond switching etc. The content of inactive FIX in a given composition can be determined by way of measurement of specific FIX-activity, which is lower in the presence of inactive FIX. Fractions containing only inactive FIX will not have any specific FIX activity at all.

In the experimental part, the inventors could here show that a fraction of approximately 25% of vitamin K-dependent protein could be separated off during the first anion exchange step (load plus elution) which was completely inactive. That shows clearly that the load material, as originating from e.g. recombinant production of FIX in CHO cells, comprises approximately 25% inactive FIX, which should preferably not be comprised in the final pharmaceutical preparation. In a preferred embodiment of this invention, the Vitamin K binding protein is selected from a FIX, FVII or FX, recombinantly produced in CHO cells, most preferably FIX, recombinantly produced in CHO cells. After separating the inactive Vitamin K dependent protein by way of the present inventive purification scheme from the active Vitamin K dependent protein, the resulting preparation is enriched in active Vitamin K, preferably essentially free of inactive Vitamin K.

The present chromatographic method on an Anion Exchange Resin thus allows the separation of active and inactive rFIX (full length) polypeptides.

Also preferred for the elution step (b) are the following embodiments, wherein preferred combinations of conductivity, Ca concentration and pH are reflected on the basis of the enclosed experiments:

| Ca mM | pH. | cond mS/cm (25° C.) |
|---|---|---|
| 1 | 7.0 | 18.6 |
| 1 | 7.0 | 19.8 |
| 1 | 8.0 | 21.2 |
| 1 | 8.0 | 22.4 |
| 1 | 6.3 | 23 |
| 1 | 8.75 | 23 |
| 2 | 7.0 | 15.8 |
| 2 | 7.0 | 16.9 |
| 2 | 8.0 | 18.3 |
| 2 | 8.0 | 19.5 |

-continued

| Ca mM | cond mS/cm (25° C.) | pH |
|---|---|---|
| 2 | 9.0 | 20.9 |
| 2 | 9.0 | 22.0 |
| 3 | 7.0 | 14.0 |
| 3 | 7.4 | 14.0 |
| 3 | 8.0 | 15.5 |
| 3 | 8.0 | 16.7 |
| 3 | 9.0 | 18.2 |
| 3 | 9.0 | 19.2 |

| Ca mM | cond mS/cm (25° C.) | pH |
|---|---|---|
| 1 | 19.8 | 7.0 |
| 1 | 19.8 | 7.45 |
| 1 | 21 | 7.5 |
| 1 | 21 | 7.85 |
| 1 | 23 | 8.3 |
| 1 | 23 | 8.75 |
| 2 | 16.9 | 7.0 |
| 2 | 16.9 | 7.45 |
| 2 | 20. | 8.2 |
| 2 | 20. | 8.65 |
| 2 | 20.9 | 8.55 |
| 2 | 20.9 | 9.0 |
| 3 | 14 | 7.0 |
| 3 | 14 | 7.4 |
| 3 | 16.0 | 7.75 |
| 3 | 16.0 | 8.2 |
| 3 | 18.2 | 8.55 |
| 3 | 18.2 | 9.0 |

| Ca mM | pH. | cond mS/cm (25° C.) |
|---|---|---|
| 1 | 7.0 | 18.2 |
| 1 | 7.0 | 20.4 |
| 1 | 8.0 | 21.7 |
| 1 | 8.0 | 22.9 |
| 1 | 8.05 | 23 |
| 1 | 8.9 | 23 |
| 2 | 7.0 | 15.3 |
| 2 | 7.0 | 17.5 |
| 2 | 8.0 | 17.9 |
| 2 | 8.0 | 20.1 |
| 2 | 9.0 | 20.4 |
| 2 | 9.0 | 22.6 |
| 3 | 7.0 | 14.7 |
| 3 | 7.6 | 14.0 |
| 3 | 8.0 | 15.0 |
| 3 | 8.0 | 17.2 |
| 3 | 9.0 | 17.6 |
| 3 | 9.0 | 19.8 |

| Ca mM | cond mS/cm (25° C.) | pH |
|---|---|---|
| 1 | 20.4 | 7.0 |
| 1 | 20.4 | 7.9 |
| 1 | 22 | 7.62 |
| 1 | 22 | 8.5 |
| 1 | 23 | 8.05 |
| 1 | 23 | 8.9 |
| 2 | 17.5 | 7.0 |
| 2 | 17.5 | 7.85 |
| 2 | 19 | 7.75 |
| 2 | 19 | 8.45 |
| 2 | 20.5 | 8.15 |
| 2 | 20.5 | 9.0 |
| 3 | 14.7 | 7.0 |
| 3 | 14 | 7.65 |
| 3 | 16.5 | 7.7 |
| 3 | 16.0 | 8.55 |
| 3 | 17.6 | 8.15 |
| 3 | 17.6 | 9.0 |

The hatched areas of the enclosed figures can also be determined mathematically, on the basis of the enclosed experiments.

Calculation of FIX Ag [%] in Post Elution $$\text{Log}(\text{FIX\_Ag}[\%] \text{ Post Elution}) = 0.150456*(\text{Elution\_pH}) - 0.0582981*(\text{Conductivity of Elution [mS/cm]}) - 0.166317*(\text{Ca-concentration Elution [mM]}) - 0.514886*(\text{Wash2\_pH}) - 0.333007*(\text{Wash2\_LF[mS/cm]}) + 0.0445826*(\text{Wash2\_pH})*(\text{Wash2\_LF[mS/cm]}) + 5.90989$$

(LF=conductivity)

The following describes a particularly preferred embodiment:

The mixture of polypeptides is loaded onto the Anion Exchange resin under conditions that allow binding of the target molecules (e.g. neutral pH, NaCl<220 mM). The selective elution is performed with 2 mM $CaCl_2$, 180 mM NaCl at pH 8.0. Approximately 25% of inactive rFIX is not eluting from the column under these conditions, active rFIX is eluting. In particular, the full-length inactive FIX is separated from active FIX in this step.

For the parameters calcium, pH and conductivity a "design of experiments" (DOE) study was performed to investigate the robustness and borders of the selective elution procedure (see examples). The experiments and the calculated model resulted in a parameter range for pH, conductivity and calcium concentration for the elution buffer that assure a robust separation of active and inactive FIX species during the elution model. The parameter ranges obtained from the experiments and model are calculated for a 3S range (mean value+/−s standard deviations of the center point runs) saying that 99.7% of experiments performed with that parameter setting will result in a robust separation of the active and inactive FIX species. To additionally separate truncated forms of FIX, the herein described "wash 2" step is particularly suitable.

Thus, the present invention also encompasses in a preferred embodiment an elution step (b), with parameter combinations chosen from the 3S range around the mean value shown in either one of FIGS. 1, 2a, 2b, 2c, 3a, 3b, or 3c.

Importantly, the model also shows that the selectivity of the elution procedure is lost when the calcium concentration is increased beyond the given ranges, and provides particularly advantageous parameter combinations that maintain the selective elution behavior.

2. The method according to item 1, wherein after the loading step one or more washing steps (1), (2) and/or (3) with a washing buffer (1), (2) and/or (3) in the absence of a divalent cation but in the presence of a counter anion is/are performed.

Preferred counter-anions are: chloride (most preferred), acetate, phosphate, sulfate, carbonate, though not limited to these.

3. The method according to item 1 or 2, wherein at least one of the loading buffer and/or washing buffer, has/have a pH that is at least 0.5 pH units lower than the pH of the eluant of step (b), preferably wherein either the loading buffer and/or the buffer in wash step (2) has/have a pH that is at least 0.5 pH units lower than the pH of the eluant of step (b).

To separate the inactive forms of the Vitamin K dependent proteins from the active forms, the above described pH shift is not necessary as long as the specific parameter conditions described herein are maintained.

4. The method according to any one or more of items 1 to 3, wherein the eluant in step (b) has a conductivity that is higher than the conductivity of the loading buffer in step (a) and the optional washing buffer and wherein the supplemented eluate in step (c) has a conductivity that is lower than the conductivity of the eluant in step (b).

In a preferred embodiment, the conductivity of the elution buffer is between 14 and 23 mS/cm (RT), preferably 19-20 mS/cm (RT). If the optional wash step 2 is performed ("acidic wash"), the conductivity is preferably between 14 and 19 mS/cm (RT), more preferred between 16 and 18 mS/cm (RT) whereby in all cases the requirement of item 4 above and the described ranges for parameters above (i.e. "h" area of figures) should be fulfilled.

5. The method according to any one of items 1 to 4, wherein the first and second anion exchange resin materials each have a positively charged group which is independently selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

6. The method according to any one of items 1 to 5, wherein the first and second anion exchange resin materials each carry a primary amine as ligand which is independently selected from the group, consisting of aminohexyl, benzamidine, lysine, and arginine.

7. The method according to any one of items 1 to 6, wherein the Vitamin K dependent protein is a divalent cation binding, preferably a calcium binding protein. A "calcium binding protein" is a protein that participates in e.g. calcium cell signaling pathways by binding to $Ca^{++}$, Calcium binding of Vitamin-K dependent proteins is e.g. necessary for binding of the protein to negatively charged cell surfaces e.g. of activated blood platelets, or e.g. for cell signalling 8. The method according to any one of items 1 to 7, wherein the vitamin K-dependent protein of this invention is preferably characterized by the existence of specific glutamate residues in protein regions, widely known as Gla domains, which are carboxylated to carboxyglutamate by a cascade of enzymes, in particular gamma-carboxylase and vitamin-K-oxidoreductase, with vitamin K as a co-enzyme. The reaction is catalyzed by a Vitamin-K dependent carboxylase that requires oxygen, carbon dioxide and the reduced form of Vitamin K. Vitamin K is recycled by a Vitamin K epoxide reductase (VKOR).

9. The method according to any one of items 1 to 8, wherein the Vitamin K dependent protein is selected from the group, consisting of Factor II, Factor VII, Factor IX, Factor X, Protein C, and Protein S, particularly preferred from the group consisting of Factor IX (FIX), Factor VII (FVIIa) and Factor X.

Any one of the above proteins can be derived either from a natural source, e.g. plasma, or from recombinant technologies.

Most preferred, the present invention concerns the purification of FIX, and in particular recombinant FIX, even more preferred the "downstream" purification of recombinant FIX which was produced by recombinant expression in CHO cells.

10a. The method according to any one of items 1 to 10 wherein the pH in step (a) is 6.8 to 7.5, preferably 7.0 to 7.4, for a case where an optional wash step is performed and its pH is 5.5 to 6.5, preferably 5.9 to 6.1 in a case where the optional wash step is not performed, 10b The method according to any one of items 1-10, wherein the pH of the optional wash step (3) is between 7.0 and 8.2, preferably between 7.3 to 8.0, even more preferred 7.3 to 7.5.

A particular preferred embodiment has the following steps:
  Loading of an anion exchange column with the cell culture supernatant from production of recombinant FIX, FVII or FX, in the absence of divalent cations, at a pH of 7.0-7.4,
  Performing a first wash, a second wash with a pH of approximately 5.5-6.5 and a conductivity of 16.5-19 mS/cm (25° C.) and a third wash with a pH of 7.3 to 7.5,
  Eluting with an elution buffer comprising 1-3 mM Ca, 17-22 mS/cm (25° C.) and a pH of 7-9, preferably all selected according to the inventive parameter ranges,
  Optionally performing an Solvent/Detergent (S/D) step for virus inactivation,
  Optionally diluting to lower the conductivity to preferably 15-18 mS/cm (25° C.),
  Increasing the concentration of $Ca^{++}$ to 6 mM and adjust the pH to 7.6-7.8,
  Loading a second anion exchange column with the diluted eluate pool and, Collecting the flow through, 11. The method according to item 10, with one or more wash steps between loading and elution at conditions that assure binding of the active product, eg. at a pH of 6.0-8.0 and a conductivity of less than 200 mM NaCl.

12. The method according to any one of items 1 to 10, wherein the pH in the optional wash step (1) is at 7.3 to 7.5, and the pH of the optional wash step (2) is preferably 5.5 to 6.5, preferably 5.9 to 6.1.

13. The method according to any one of items 1 to 12, wherein the elution buffer (i.e. eluant) in step (b) contains 2 mM Calcium and has a pH of ~8.0 and conductivity of 18-19 mS/cm (25° C.), obtained by an addition of 180 mM NaCl, 14. A method according to any of item 1-13 above, particularly according to item 3, wherein the pH of the loading buffer in loading step (d) is higher than either the pH of the loading buffer in loading step (a) or the pH of the wash, which follows after loading (a).

The "wash which follows after loading (a)" in the context above and as also mentioned below, refers here to the "acidic wash" or wash 2.

The presently described "acidic" wash is suitable to separate truncated forms of Vitamin K dependent proteins, e.g. FIX, from full-length proteins.

15. A method according to any of items 1-14 above, particularly according to item 3, wherein the conductivity in the loading step (d) is equal to or lower than the conductivity of the wash, which follows after loading (a).

16. A method according to any of items 1-15 above, particularly according to item 3 above, wherein the concentration of $Ca^{++}$ of the loading buffer in step (d) is higher than the concentration of $Ca^{++}$ in the elution buffer of step (b).

17. The method of any of items 1-16, wherein the step of providing the obtained eluate pool with a low conductivity is carried out by dilution with an appropriate dilution buffer, alternatively by changing the buffer composition, or alternatively by dialysis, diafiltration or gel-filtration.

18. A Vitamin K dependent protein, as obtained by the method according to any one of items 1-17 above.

19. (r)FIX, obtained by the method according to any one of items 1-17 above.

20. (r)FIX according to item 19, with a specific activity of at least 270 I.U./mg FIX Ag, preferably a specific activity of 270 to 350 I.U./mg FIX Ag, more preferred a specific activity of 270 to 320 I.U./mg FIX Ag, particularly preferred with a specific activity of 280 to 300 I.U./mg FIX Ag.

21. Pharmaceutical composition comprising (r)FIX as defined in item 19 or 20, with a CHO HCP reduction ratio of about 2.5-3 log reduction.

The 2.5-3 log reduction is the log of the overall reduction of CHO HOP. A CHO HCP reduction has been shown as 229 (from step 1 to step 2) and 1.75 (from step 2 to step 3), i.e. 1.75×229=approx. 440, the log thereof would be 2.6.

22. Pharmaceutical composition comprising (r)FIX as defined in item 19 or 20, and/or according to item 21, with a CHO HCP impurity of less than 50 µg/mg FIX Ag, preferably less than 20 µg/mg FIX Ag, even more preferred less than 10 µg/mg FIX Ag.

23. Pharmaceutical composition comprising (r)FIX as defined in item 19 or 20, and/or according to item 21 or 22, wherein the composition comprises less than 10 pg/ml CHO DNA, preferably less than 5 pg/ml CHO DNA, even more preferred less than 1 pg/ml CHO DNA.

24. Pharmaceutical composition comprising (r)FIX as defined in item 19 or 20, and/or according to any one of items 21-23, wherein the (r)FIX composition comprises less than 1 mU FIXa (activated FIX) activity/unit FIX clotting activity, preferably less than 0.75 mU FIXa activity/unit FIX clotting activity, more preferred less than 0.5 mU FIXa activity/unit FIX clotting activity, even more preferred less than 0.3 mU FIXa activity/unit FIX clotting activity.

1 mU FIXa activity/unit FIX clotting activity is equivalent to 0.1% chromogenic activity per IU/ml FIX clotting activity (see assay method as described below)

25. Pharmaceutical composition comprising (r)FIX as defined in any one of items 19 or 20, and/or according to any one of items 21-24, wherein the composition is enriched in an active, single chain and full length FIX species.

Preferably, the resultant composition is essentially free of inactive (full-length) FIX.

26. A kit comprising means for carrying out the method according to any one of items 1-17.

27. (r)FIX composition, obtainable by the method of any one of item 1-17, wherein the (r)FIX composition comprises less than 1 mU FIXa (activated FIX) activity/unit FIX clotting activity, preferably less than 0.75 mU FIXa activity/unit FIX clotting activity, more preferred less than 0.5 mU FIXa activity/unit FIX clotting activity, even more preferred less than 0.3 mU FIXa activity/unit FIX clotting activity.

28. (r)FIX composition according to item 27, further characterized by one or more of the features as defined in any one of items 19-25.

29. (r)FIX composition, wherein the (r)FIX composition comprises less than 1 mU FIXa (activated FIX) activity/ unit FIX clotting activity, preferably less than 0.75 mU FIXa activity/unit FIX clotting activity, more preferred less than 0.5 mU FIXa activity/unit FIX clotting activity, even more preferred less than 0.3 mU FIXa activity/unit FIX clotting activity.

30. (r)FIX composition according to item 29, further characterized by one or more of the features as defined in any one of items 20-25.

Thus, the present invention also relates to purified Vitamin K dependent proteins obtainable by the above method, and to a kit comprising means for carrying out the above method. The present invention accordingly also relates to FIX, preferably recombinant FIX, which is obtainable by the inventive method or has been obtained by the inventive method. The present invention also relates to FIX or FIX compositions, preferably recombinant FIX or FIX compositions with a low content of FIXa. A FIX or FIX composition can be obtainable by or has been obtained by the inventive method and is characterized by their particularly low contents of inactive FIX.

DETAILED DESCRIPTION OF THE INVENTION

In one aspect, the present invention relates to method for the purification of a vitamin K-dependent protein comprising the steps of:
(a) loading an anion exchange resin material (in the following also "the first anion exchange resin material") with the vitamin K-dependent protein in a loading buffer in the absence or low concentration of divalent cations, optionally followed by one to three wash steps;
(b) eluting the divalent cation binding protein with an eluant comprising a divalent cation and a counter-anion to form an eluate containing vitamin K-dependent protein, wherein:
1-3 mM calcium is comprised in the eluant
the eluant has a conductivity of 14-23 mS/cm (25° C.) and,
the pH of the eluant is between 7.0 and 9.0.

In a further preferred embodiment, the method for purification further comprises the following steps:
(c) diluting the obtained eluate pool, ((1) to optionally lower the conductivity), and increasing the concentration of the calcium;
(d) loading a second anion exchange resin material with the eluate as obtained after step (c); and
(e) collecting the flow-through containing the divalent cation binding protein.

The present inventive method preferably uses a procedure on two anion exchange columns with the first column being operated in a product binding mode, and the second column being operated in a product non-binding mode.

The principle of the procedure requires in a preferred embodiment contacting (i.e. loading) the Vitamin K dependent protein (e.g. rFIX) solution with (on) an anion exchange resin at a neutral or acidic pH (pH=6.8-7.5, pref. 7.0-7.4, e.g. 7.0-7.2) in the presence of a chelator, e.g. EDTA. EDTA can be preferred if the product yield shall be further improved. EDTA can improve the binding of the divalent cation binding protein, e.g. FIX. In a preferred embodiment, after one or more washes (at e.g. a pH as defined more in detail below), the product is eluted with a buffer containing 1-3 mM calcium (with a pH and conductivity in a very specific range as defined above). The resulting Vitamin K dependent protein, e.g. rFIX, contained in the eluate pool has a low content of inactive FIX and is additionally and surprisingly enriched in active, full length single chain FIX species.

The obtained eluate pool is then—in a preferred embodiment—diluted to lower the conductivity and increase the calcium concentration. The diluted solution has a pH of e.g. 7.6-7.8. The conditioned eluate pool of the first anion exchange purification step is then transferred (e.g. pumped) onto the second anion exchange column where the Vitamin K dependent protein, like e.g. rFIX, does not bind under the conditions applied (in particular presence of increased concentrations of divalent cations, and slightly basic pH and a conductivity of about 15-21 mS/cm (RT)), whereas protein impurities do bind. The resulting vitamin K-dependent protein, e.g. rFIX, contained in the column effluent of the second anion exchange purification has a high purity and high specific activity. In particular, it has a particularly low content of inactive FIX.

The present invention is further explained by the following figures:

FIG. 1: Evaluation of design space of the capture step ("CPN") elution buffer in terms of removal capacity of inactive FIX forms (variable parameters: calcium and conductivity, pH=constant).

Evaluation of data of a small scale robustness study for the capture step DOE study designed and evaluated with the software tool Mode (version 9.1). In this graph, the FIX antigen content in the high salt wash (post elution=fraction was investigated considering the parameters conductivity and calcium content of the high salt wash buffer). The hatched area indicates a design space for the buffer composition that would lead to a good removal capacity for the inactive full length FIX antigen. In the further areas, inactive FIX polypeptides could co-elute with the main product pool.

Contour plot of data evaluation within parameter ranges of 1-3 mM (Calcium) and 14-23 mS/cm (25%) for conductivity at pH=8.

Figure 2:
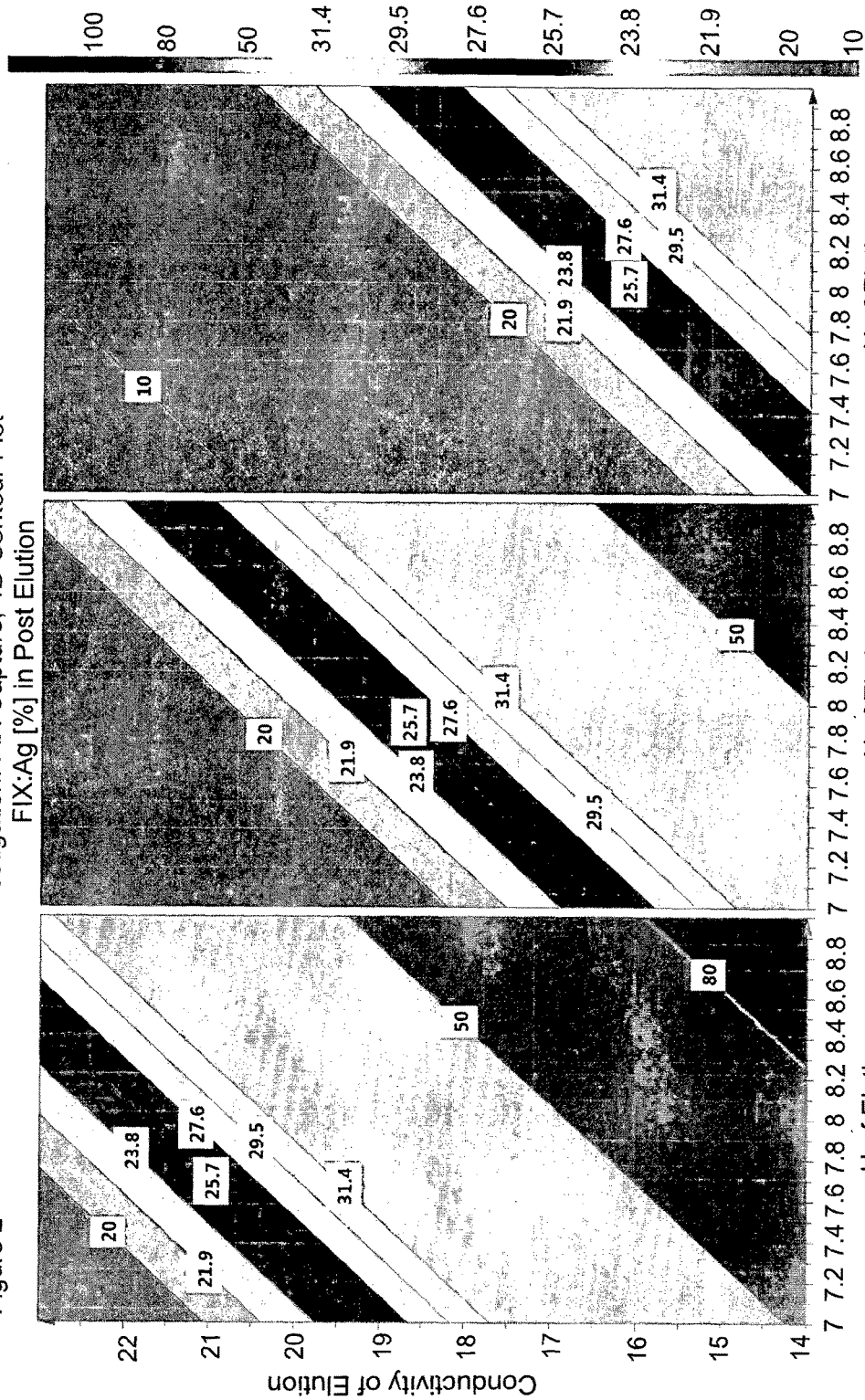

FIG. 2: Evaluation of design space of the capture step (CPN) elution buffer in terms of removal capacity of inactive FIX forms (variable parameters: calcium and conductivity, pH=7-9).

FIG. 2A: $Ca^{++}$=1 mM
FIG. 2B: $Ca^{++}$=2 mM
FIG. 2C: $Ca^{++}$=3 mM

Figure 3:
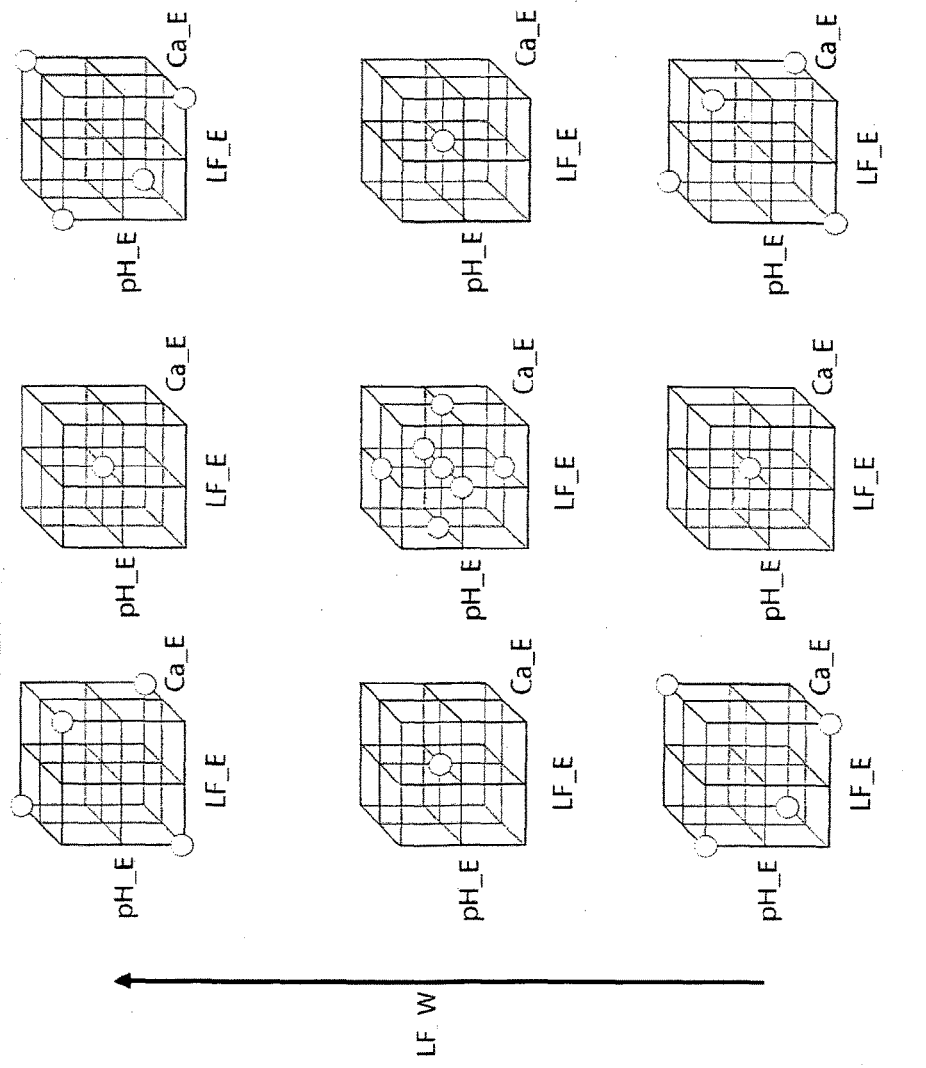

FIG. 3: Overview of tested process parameters at CPN step including testing ranges for the lab scale DOE experiments As is derivable from the present experimental data, as shown in the figures and example part, the parameter "calcium concentration" of the elution buffer is very relevant for the separation, the parameters pH and conductivity are important and interfere with the elution as the elution takes place on an Anion Exchange resin, pH and conductivity are responsible for the shift of the window where efficient separation during the elution can be done successfully. Very surprisingly, it is possible to perform a separation of inactive Vitamin-K dependent protein from the load at low $Ca^{++}$ concentrations of 1-3 mM.

The term "in the absence of divalent cations" as used herein refers to the absence of free divalent cations in the buffer, wherein divalent cations that are bound to a protein or complexed e.g. by a chelator, e.g. EDTA, may be present. The term "at a low concentration of divalent cations" refers to a divalent cation concentration in the μM range, in particular a concentration of 1000 μM at most, preferably 800 μM at most, even more preferred 500 μM at most. For this application the term "in the absence of divalent cations" is meant to also encompass the above definition for "at a low concentration of divalent cations". As already mentioned above, protein bound calcium, e.g. EDTA bound calcium can be tolerated in one embodiment. If the calcium is bound to a protein, it is considered "inactive" calcium in the context of this invention. It does then not interfere with product binding. Free calcium, on the other hand, could interfere with product binding.

Loading (a) of the first anion exchange resin material with the Vitamin K dependent protein in a loading buffer in the absence of divalent cations can be carried out by any method known in the art. In particular, conditions suitable for loading the Vitamin K dependent protein to the anion exchange resin material are well known to a person skilled in the art. The specific conditions for the conductivity of the loading buffer that allow binding of the product depend on the particular properties of the protein and the anion exchange resin material used (e.g. ligand density, ligand presentation, etc.). Divalent cations bind to proteins in regions that are usually highly acidic (i.e. negatively charged). The negative charges are masked when the divalent cation is bound. However, by loading the anion exchange material with the Vitamin K dependent protein in the absence of divalent cations, e.g. by stripping off the bound divalent cation by a chelator, e.g. EDTA, the protein carries highly negatively charged patches on the surface that allow strong binding to an anion exchange ligand. The conditions for loading a protein onto an anion exchange resin material further always require a balance between pH and the concentration of the counter-ions, e.g. $Cl^-$. The chemistry of the counter-ion also influences the elution behavior, e.g. $Cl^-$ carries one negative charge, and phosphate at neutral pH carries two negative charges. The latter can have a higher eluting power compared to $Cl^-$, even when the conductivity is lower.

The loading of Anion Exchange column 1 (i.e. step (a)) is preferably performed at a pH of 6.8-7.5, preferably 7.0-7.4, followed by a wash 1 at a pH of 7.3-7.5 to complete loading, a wash 2 at acidic conditions (pH 5.5-6.5, preferably 5.8-6.2, more preferably 5.9-6.1). In a further embodiment an optionally wash 3 (low conductivity wash, this is the wash which is carried out directly before elution) at pH 7.0-8.2, preferably 7.3-8.0, e.g. pH 7.3-7.5 to prepare the column for elution can be carried out. The elution is performed at a pH of 7.5-8.5, more preferably 7.8-8.2. In one embodiment of the present invention, the pH of the elution buffer is at least 0.5 pH units higher than the pH of the preceding wash 2 (high conductivity wash, see conductivity conditions as described above). This second, "acidic" high conductivity wash still has a conductivity which is lower than the conductivity of the elution. However, as is clear from the enclosed hatched area as well as the above description of preferred parameter ranges, it is possible to obtain a good separation of inactive from active FIX, even if the pH is kept constant.

In one embodiment, the loading step of the first anion exchange is carried out at a neutral to slightly acidic pH, e.g. at a pH of 6.8-7.5, preferably 7.0 to 7.4, if the optional washing step(s) is (are) performed. Preferably this loading step is followed by a first wash at pH=7.3-7.5 to complete loading, a second wash at acidic conditions (pH 5.5 to 6.5, preferably 5.8 to 6.2) and a wash 3 at a pH of 7.3-7.5 to prepare the column for elution. The pH of the loading step of the first anion exchange column is set at 5.5 to 6.5, more preferred at pH 5.9-6.1, if the optional washing step(s) is (are) not performed. In one embodiment the pH is increased, preferably by at least 0.5 pH units, before the elution step is carried out. This increase can occur at all stages, e.g. from the loading step directly to the elution step, if no wash steps are carried out in between. In an alternative embodiment, the pH increase occurs after an acidic wash, as described above. The elution is—as described below—preferably carried out at the pH as described in the preferred embodiments of parameter ranges for the elution step.

In a case where only one wash step is carried out, i.e. wash step (1), this wash step will be carried out without addition of salt; consequently, the pH is of not of immediate importance in the wash step.

In one preferred embodiment, where two wash steps are carried out, i.e. wash steps (1) and (21 or where only the stringent wash step (2) (see also below) is carried out, this loading buffer could have a pH in the neutral to slightly acidic area, as defined above, though that would be allowable according to the inventive principles only if the second wash step (i.e. wash step 2) had a lower pH of 5.5 to 6.5, or 5.9-6.1. If the loading step was already carried out at this lower pH, than the wash step (2) would preferably also have this lower pH. Wash step (2) in a preferred embodiment is carried through at a high conductivity, as defined above.

In a further preferred embodiment, where three wash steps are carried out, i.e. wash steps (1), (2) and (3), the wash step (3) would preferably not contain any salt; consequently, the pH in this step would not be relevant, as long as the above conditions as mentioned for the case with two wash steps are provided for and the pH is increased in the elution step by at least 0.5 pH units, compared preferably to the loading and/or the wash step (2). Wash (3) is preferably a low conductivity wash (in that case, step c(1) need not be carried out, if the conductivity of the resultant eluate is already low).

In a particularly preferred embodiment, the pH in the wash step (3) can already be increased to the level of the pH of the elution step. Thus, the preferred pH of wash step (3) is between 7.0 and 8.2, preferably between 7.3 and 8.0, even more preferred at 7.3-7.5. If the wash step (3) is performed at this particular pH condition the present inventors found that the degree of impurities which are comprised in the eluted desired product is further reduced compared to a situation where no wash step (3) is performed or where said step is performed at a different pH, e.g. at a pH which is still as low as the pH used during loading and/wash steps (1) and (2). The inventors believe, though they do not wish to be bound to that hypothesis, that adjusting the pH of the wash step (3) to the same pH as the elution avoids a pH gradient during elution. A pH gradient during elution could be a source of interference which allows some impurities to be co-eluted with the product. Wash 3 as described above conditions the column advantageously for elution. A high pH and low conductivity of this wash prevent co-elution of impurities during the following elution.

Even more preferred, the wash step (3) should have a conductivity, and in particular an elution power which is very low or even close to zero. Such a very low conductivity would be preferably at 1-15 mS/cm (RT), more preferably below 5 mS/cm (RT).

In a preferred embodiment, a solution comprising proteins, the desired product, and all compounds of the cell culture media including amino acids, vitamins, sugars, trace metals etc (including KCl, NaCl, Ca, ca. 13 mS/cm (RT)) is the load material in loading step (a). After the loading step, a washing step 1 is preferably carried out which is then completing the loading (preferably close to or at neutral pH and at a low conductivity). Thereafter, preferably a second washing step 2 follows, which is considered a stringent wash, and is preferably carried out with a low pH and 150 to 210, preferably 170 to 190 mM, most preferred 180 mM (if carried out with NaCl, preferred conditions for different salts would be within the knowledge of the person skilled in the art), followed in a further preferred embodiment by a washing step 3 which is preparing the loaded column for the elution. This third wash step is preferably carried out at a low conductivity and at a pH as defined above. This washing step has the major task to reduce the conductivity in the column and bring the pH back to neutral as the previous wash was at low pH, and even bring the column close to the pH of the elution, as explained above. These measures prepare the column for the pseudo-affinity elution with Calcium and prevent co-elution of impurities in the interface between elution buffer and wash-2 buffer. The elution is preferably carried out with a buffer containing calcium and 150 to 210, preferably 170 to 190 mM and most preferred 180 mM NaCl. The content of the counter-ions, e.g. NaCl, is adjusted to obtain the desired conductivity, as described above for the preferred parameter ranges for elution from the first anion exchange column. Other counter anions would be possible, in addition to the above chloride (most preferred), e.g. acetate, phosphate, sulfate, carbonate, though not limited to these.

Further, suitable loading buffers for loading a Vitamin K dependent protein to an anion exchange material in step (a) of the method of the present invention, providing conditions under which the Vitamin K dependent protein is bound to the anion exchange material are well known in the art. For example, the loading buffer can have a pH of pH 6.8 to 7.5, preferably of pH 7.0 to 7.4, if an optional washing step (s) is (are) carded out, as explained above. It may contain any salt concentrations suitable for binding the Vitamin K dependent protein to the anion exchange resin material which may be easily determined by a person skilled in the art. In a preferred embodiment, the loading buffer may contain a chelating agent, e.g. EDTA, preferably 0.5 to 10 mM EDTA, more preferred 1 to 5 mM EDTA, preferably approximately 2 mM EDTA. Alternative possible chelating agents can also be used and are well known to a person skilled in the art. A loading buffer containing the Vitamin K dependent protein which may be applied to the anion exchange resin material in the method of the present invention may contain for example 20 mM MES and 2 mM EDTA. MES is an example for a buffering agent for pH 6; for pH 7 and above it would e.g. be possible to use Tris buffer. As the loading material is in a preferred embodiment a cell culture supernatant, e.g. from recombinant production in a CHO cell line, which is basically buffered by carbonate and amino acids, a loading buffer must not necessarily be present.

The method of the present invention preferably comprises the step of washing the loaded anion exchange resin material with a washing buffer in the absence of divalent cations. This washing step can be carried out by any method known in the art. Suitable washing buffers for washing impurities off the anion exchange material essentially without eluting the Vitamin K dependent protein are well known in the art. For example, the washing buffer has a pH which is at least 1.0 or at least 0.5 pH units lower than the pH of the loading buffer and is preferably 5.5-6.5, preferably 5.9-6.1. It may contain any salt concentrations suitable for washing the anion exchange resin material without eluting the Vitamin K dependent protein in a significant amount which may be easily determined by a person skilled in the art. For example, the washing buffer may contain a suitable buffer agent like for example Bis-Tris, acetate buffer, citrate buffer or phosphate buffer, preferably 20 mM Bis-Tris. Preferably, the washes 1 and 3 have Iris as washing buffers while wash 2 has MES. Additionally, it may contain a chelating agent like for example EDTA, preferably 0.5 to 10 mM EDTA, more preferred 1 to 5 mM EDTA, preferably approximately 2 mM EDTA. Further, it may contain a suitable salt, e.g. salts of the following cations and anions: $K^+$, $Na^+$, $Li^+$, $NH_4^+$ and anions like chloride, phosphate, sulfate, carbonate, acetate, for regulating the conductivity of the washing buffer, like for example NaCl, which may be present in a concentration of ≤200 mM, preferably from 100 mM to 200 mM, more preferably from 150 mM to 200 mM, more preferably from 170 mM to 190 mM, and most preferably from 175 mM to 185 mM. In another preferred embodiment of the present application, the washing buffer contains 100 to 200 mM NaCl. The absolute value for the salt concentration depends on the Vitamin K dependent protein to be purified, wherein it is within the knowledge of the person skilled in the art to determine which Vitamin K dependent proteins require lower or higher salt concentrations to get the optimal purity.

Preferably, according to the present method for purification of Vitamin K dependent proteins, a second wash step is carried out after the above-mentioned first wash step. This wash step, if being the wash directly before elution, is carried out at a low conductivity. This conductivity is preferably lower than the conductivity in the loading and the first wash step. Even more preferably, a third wash step can be performed. This embodiment has been described above in detail.

Eluting the Vitamin K dependent protein with an eluant comprising calcium can be carried out by any method known in the art. In particular, suitable eluants containing suitable counter-cations are well known in the art. The elution buffer can have a pH which is higher than the pH of the wash buffer. The pH is preferably increased by at least 0.5, preferably 1.0 pH units. The elution buffer must have a pH as selected in accordance with the preferred combination embodiments shown herein, in particular those embodiments within the hatched area of FIGS. 1-3. It contains those salt concentrations as determined by the present inventors to be suitable for eluting the Vitamin K dependent protein from the first anion exchange resin material without eluting impurities, particularly inactive FIX, in a significant amount.

In particular, it is now possible, by working in the parameter ranges for the parameters of pH, conductivity and $Ca^{++}$ concentration for the elution step from the first anion exchange column, to separate as much as 25% inactive Vitamin K dependent protein from the active Vitamin K dependent protein, thus enriching the resultant Vitamin K dependent protein in its content of active Vitamin K dependent protein, preferably to a preparation which is essentially free of inactive forms, particularly free of inactive full length forms For example, the elution buffer may contain a suitable buffer agent like for example HEPES, Tris, preferably 20 mM Tris, Tris/acetate, histidine, Gly-Gly, MOPS, or tricine, at concentrations ranging typically from 5 to 50 mM. It may also contain a suitable salt, e.g. salts of the following cations and anions: $K^+$, $Na^+$, $Li^+$, $NH_4^+$ and anions like chloride, phosphate, sulfate, carbonate, acetate, for regulating the conductivity of the buffer, like for example NaCl, which may be present in a concentration of 120-205 mM.

The following is a list of particularly preferred buffers:
Tris: buffers at pH=8.06±1.0,
HEPES: buffers at pH=7.7±1.0,
MOPS; buffers at pH=7.3±1.0,
Tricine: buffers at pH=8.3±1.0,
Histidine: buffers at pH=7.6±1.0,
Gly-Gly: buffers at pH=7.4±1.0,
Bis-Tris: buffers at pH=6.35±1.0,
ACES (N-(2-Acetamido)-2-aminooethanesulfonic acid): buffers at pH=7.0±1.0,
ADA (N-(2-Acetamido)-iminodiacetic acid): buffers at pH=7.0±1.0,
MES: buffers at pH=approx.

The elution buffer may also contain a suitable salt for regulating the conductivity of the washing buffer, like for example NaCl, which may be present in a concentration of 120-205 mM.

After the elution step, the eluate pool obtained is diluted to lower the conductivity and the concentration of calcium, preferably the calcium concentration is increased. This measure provides conditions that prevent binding of the product to the second Anion Exchange resin and facilitates binding of host cell proteins. Such a dilution is known to a person skilled in the art and is conducted according to well known methods. For example, the addition of one column volume dilution buffer increases $Ca^{++}$ and slightly reduces the conductivity. The diluted solution preferably has final pH of 7 to 8, more preferably 7.5 to 7.9.

The person skilled in the art understands that further procedures to provide the obtained eluate pool with the decreased conductivity would also fall under the definition of diluting the eluate pool to lower the conductivity. Thus, further possibilities to lower the conductivity of the eluate pool would be changing the buffer composition, e.g. by dilution with a low salt buffer or by dialysis, or by using diafiltration.

As used herein, the term "anion exchange resin material" does not underlie a specific restriction. According to the present invention, the first and second resin includes any material suitable for anion exchange chromatography known in the art, like for example an agarose based chromatography material, e.g. sepharoses like Fast Flow or Capto, polymeric synthetic material, e.g. polymethacrylate like Toyopearls, polystyrene/divinylbenzene, e.g. Poros, Source, or cellulose, e.g. Cellufine. In a specific example of the present invention, the first and second anion exchange resin material is sepharose, which is based on modified agarose, the polysaccharide chains of which are crosslinked to form a three-dimensional network. In a preferred embodiment, the first and second anion exchange resin materials include, but are not limited to resins that carry a primary amine as ligand, e.g. aminohexyl sepharose, benzamidine sepharose, lysine sepharose, or arginine sepharose. In another preferred embodiment, the first and second anion exchange resin materials include, but are not limited to resins having a positively charged moiety at neutral pH, such as alkylaminoethane, like diethylaminoethane (DEAF), dimethylaminoethane (DMAE), or trimethylaminoethyl (TMAE), polyethyleneimine (PEI), quaternary aminoalkyl, quaternary aminoethane (QAE), quaternary ammonium (Q), and the like. In a particularly preferred embodiment the anion exchange resin material is Q-Sepharose Fast Flow (Q-Sepharose FF). According to the method of the present invention, the first and second anion exchange resin materials may be the same or may be different.

The loading buffer (step d) for the second Anion Exchange step can be the same as above for the first anion exchange step. The difference between the two anion exchange steps as provided according to the present invention is essentially the following:
a) The first anion exchange column is loaded with the starting material, i.e. in a preferred embodiment with the cell culture material. This is a highly impure starting material. The second anion exchange column is loaded with material which has already been purified to some extent, as it is the material obtained after the elution (and supplementation) step.
b) The first anion exchange step is carried out with divalent cations, for the elution of the product, after having loaded the first anion exchange column in the absence of divalent cations.

c) The pH and the concentration of the divalent cations of the load for the second anion exchange is selected in a preferred embodiment so that the pH of load (d) is higher and the pH of either the (acidic, e.g. wash 2) wash after the load (a) or the load (a) per se if no wash steps are used. Furthermore, the conductivity of load (d) is comparable to the acidic wash, but preferably lower, if this wash is carried out. The divalent cation concentration, e.g. Ca concentration is higher in the load (d) than the elution buffer of step (b).

d) Consequently, on the first anion exchange column the product binds to the column and on the second anion exchange column the product does not bind.

The Vitamin K dependent protein according to the present invention is a divalent cation binding protein, like for example a calcium binding protein. In a preferred embodiment, the Vitamin K dependent protein is selected from the group, consisting of Factor II, Factor VII, Factor IX, Factor X, Protein C, and Protein S, particularly preferred from the group consisting of Factor IX, Factor VII and Factor X.

The starting material ("sample") for the Vitamin K dependent protein may be obtained using methods known to a person skilled in the art like, e.g. plasma derived proteins, transgenically produced proteins, or recombinantly produced proteins, for example using CHO cells. Secretory and non-secretory methods for extracting proteins from cell culture are well known to a person skilled in the art. This may include any method known in the art for (i) the production of recombinant DNA by genetic engineering, e.g. via reverse transcription of RNA and/or amplification of DNA, (ii) the introduction of recombinant DNA into prokaryotic or eukaryotic cells by transfection, e.g. via electroporation or microinjection, (iii) the cultivation of said transformed cells, e.g. in a continuous or batchwise manner, (iv) the expression of a Vitamin K dependent protein, e.g. constitutive or upon induction, and (v) the isolation of the protein, e.g. from the culture medium or by harvesting the transformed cells, in order to obtain a crude Vitamin K dependent protein. Additionally, the recombinant DNA encoding a Vitamin K dependent protein, e.g. a plasmid, may also contain a DNA sequence encoding a selectable marker for selecting the cells which have been successfully transfected with the recombinant DNA.

In a preferred embodiment of the present invention, the starting material for the inventive method is a material comprising FIX, preferably plasma comprising FIX or recombinantly produced FIX. The recombinant production of FIX is well known in the art. rFIX, which is recombinant FIX, is according to a preferred embodiment secreted in the cell culture supernatant (CCS) and this CCS is then used as a starting material for the present inventive method.

The proteins may be pre-purified to reduce impurities, for example by gel electrophoresis, chromatography, gel filtration, centrifugation, filtration, precipitation, crystallization or any other method known in the art. The term "impurity" as used herein includes any impurity originating from the production of the Vitamin K dependent protein and may include e.g. host cell protein (HCP) impurities, nucleic acid impurities, polypeptide impurities, buffer and salt impurities, impurities originating from the cell culture medium, product related impurities, such as dimers or fragments, and combinations thereof.

The inventive method as described herein allows the removal or separation of inactive and truncated forms of e.g. FIX from the active FIX product. The method also allows to control or keep the formation of product related impurities at a very low level (e.g. degradation products, product aggregation, particles). Even further, the method provides conditions to keep the amount of activated FIX (FIXa) at a particularly low level.

In addition, the method is particularly powerful in separating off process related impurities (CHO HCP, CHO DNA, media components) from the active FIX product.

A further impurity which is encountered in particular in FIX preparations, even FIX pharmaceutical preparations, is activated FIX, i.e. FIXa. It has been shown that FIXa negatively affects the desired resultant FIX preparation as it raises thrombogenicity. Thus, it is highly desirable to provide methods to reduce the content of FIXa in a FIX preparation.

The present inventive method achieves this goal by preventing the formation of FIXa in the preparation which is obtainable by the present method.

In an advantageous and surprising way, it is also possible according to the present invention to reduce the content of host cell protein (HOP), in particular CHO cell HOP if the starting material used is a recombinantly produced FIX in a cell culture or cell culture supernatant.

In a further advantageous and surprising way, it is additionally possible to reduce the content of host cell DNA, in particular CHO DNA in the composition obtainable by the present inventive method.

The above results are further to the improvements in yield and specific activity which are provided by the present invention.

In a preferred embodiment, the Vitamin K dependent protein which has been purified according to the method of the present invention has a purity with respect to host cell protein (HCP) impurities of at least 95% w/w, and most preferably at least 99.5% w/w Vitamin K dependent protein in total protein. Accordingly, in a preferred embodiment, the content of the HCP impurities in the purified Vitamin K dependent protein is less than 5% w/w, more preferably 2% w/w, more preferably less than 1% w/w, and most preferably less than 0.5%© w/w. The percentage values of the HOP impurities refer to w/w of product, i.e. the purified Vitamin K dependent protein, and can be measured, for example, by HPLC or ELISA.

Further, in another aspect of the present invention, a purified Vitamin K dependent protein is provided which is obtainable by or has been obtained by the method of the present invention or also, a kit is provided comprising means for carrying out the method of the present invention. In particular, the kit of the present invention may contain a loading buffer and/or an eluant and/or a washing buffer and/or a solution of divalent cations which are suitable for the purification of a Vitamin K dependent protein using an anion exchange resin material according to the present invention. In a preferred embodiment, the loading buffer, the washing buffer and/or the eluant are as defined above. Further, the kit of the present invention may contain a suitable anion exchange resin material.

The present invention further relates to the use of the method of the present invention as defined above and/or of the kit of the present invention as defined above for the purification of a Vitamin K dependent protein.

The present invention provides an efficient method for the purification of a Vitamin K dependent protein using anion exchange resin materials allowing a high reduction of process related impurities of the protein with concomitantly high product yields.

The eluate pool which has been diluted of the first anion exchange purification step is then loaded onto the second anion exchange column, where the Vitamin K dependent protein will not bind under the conditions applied. The resulting Vitamin K dependent protein contained in the column affluent of the second anion exchange purification has a high purity and high specific activity. Furthermore, it has a low content of (CHO) HCP, a low content of (CHO) DNA and a low content of FIXa.

The content of Factor FIXa is measured by way of its activity, expressed as percentage activity relative to Factor IX activity.

The potency (in international units, IU) of a recombinant FIX (rFIX) product, is determined using a widely known and accepted in vitro one-stage clotting assay using a reference calibrated against the World Health Organization (WHO) International Standard for Factor IX concentrate. One international unit is the amount of FIX activity present in 1 mL of pooled, normal human plasma (Barrowcliffe T W, Standardization of FVIII and FIX assays, Haemophilia 2003; 9: 397-402).

FIXa in said product is measured using an assay which is generally well known to a person skilled in the art. One example is the commercially available chromogenic FIXa kit (like Rox FIX-A, article No 950030; Rossix, MoIndal, Sweden) employing a reference calibrated against the World Health Organization (WHO) International Standard for Factor IXa. To carry out such an assay, human FX is activated to FXa by FIXa in the presence of FVIII, thrombin, calcium and phospholipids. The amount of FXa generated is measured with a specific FXa substrate, which upon cleavage will liberate p-nitroaniline in amounts that are proportional to those of FXa. The assay is very sensitive to FIXa with a lower limit of quantification of 0.10 mIU/mL.

The levels of pre-activated FIX (rFIXa) in the final product (as obtained by the present inventive method) were consistently very low. The allowed limit is set as ≤0.10% FIXa activity (chromogenic IU/mL)/FIX activity (clotting IU/mL). The actual FIXa content of 15 tested batches of the invention was however as low as ≤0.02% FIXa/FIX. All FIX preparations, which were obtained following the presently claimed purification process, had values of less than 0.02% FIXa/FIX. When a single BeneFIX lot (E94791 as comparative product available on the market) was analyzed with the same assays, the relative FIXa content was measured as 0.11%.

Taken together, the relative FIXa content of all lots was consistently low and apparently up to 10-fold lower than that of the comparative product.

In particular, the method of the present invention is based on the following general principle. Generally, binding of proteins to anion exchange resin materials is increased at lower conductivities and higher pH values. Vice versa, binding of proteins to anion exchange resin materials is decreased at higher conductivities and lower pH values. In the method of the present invention, the Vitamin K dependent protein is preferably loaded and/or washed at a low pH, as explained in detail above, which still allows binding of the Vitamin K dependent protein to the first anion exchange material and does not harm the structural integrity or the activity of the Vitamin K dependent protein. Many protein impurities will not bind to the first anion exchange resin material, and, therefore, binding of impurities to the first anion exchange resin material is greatly reduced while the product indeed does bind to the first anion exchange column. Protein impurities that do bind to the first anion exchange resin material under these conditions, and did not get washed off are prevented from co-elution by increasing the pH during elution. A possible increase of the pH in the eluant causes all proteins to bind even stronger to the first anion exchange resin material, but the calcium specifically interacts with the product causing elution.

The elution buffer of the first anion exchange column is conditioned
  to adjust the conductivity (to the ranges as described above), in particular within a specific range relative to the parameters of pH and $Ca^{++}$ concentration,
  adjust the pH to be within a specified range relative to the parameters of conductivity and $Ca^{++}$ concentration, and
  increase the concentration of Calcium (to be higher than in the load (a)) and to be between 1-3 mM, but again selected in relation to the parameters of pH and conductivity.

These measures provide the conditions for selective binding of impurities, particularly of inactive FIX, and selective non-binding and elution of the active product on the Anion Exchange resin.

According to a preferred embodiment of the method of the present invention, the eluate is further conditioned, as described herein so that only the Vitamin K dependent protein does not bind to the second anion exchange material due to the selection of parameters in the eluate. In this context, it should be noted that increasing the pH for loading in step (d) compared to the acidic wash is very atypical for a negative chromatography, i.e. an anion exchange chromatography wherein the protein to be purified is expected in the flow-through, since—as has been stated above—proteins generally bind stronger to anion exchange resin materials at higher pH values.

Importantly, by using the elution buffer for the first anion exchange resin material with 1-3 mM $Ca^{++}$, the method of the present invention surprisingly and advantageously achieves superior contents of the active Vitamin K dependent protein product by anion exchange chromatography.

Also, the optional increase of pH during the Ca-induced product elution of step (b) (elution buffer has higher pH than load buffer of step (a) or acidic wash of step (a)) and the adjustment of the load for step (d) (pH higher than acidic wash of step (a), calcium higher than eluant of step (b)) provides for a selective purification of Vitamin K dependent proteins and prevents co-elution of impurities. The loading of the second anion exchange resin material at high pH and high calcium forces impurities to bind to the second anion exchange resin material while binding of the protein to be purified is inhibited by supplementing divalent cations. According to the present invention, the above conditions result in a high purity as well as high yields of Vitamin K dependent proteins. The method of the present invention may provide a significant reduction of process related polypeptide impurities e.g. by loading the protein solution onto an anion exchange resin material at reduced pH, eluting the product with an eluant with at calcium at 1-3 mM, at a specifically selected pH and conductivity, loading the eluate onto a second anion exchange resin material under high pH, and increased concentration of calcium, but in particular by the specific parameter selection during elution, and collecting the flow-through.

The purification strategy is based inter alia on the unique biochemical properties of vitamin K dependent proteins. E.g. in the Gla-domain about 12 negative charges are focused within a short amino acid stretch. This negative charge can be neutralized or even converted to positive charge by adding divalent cations (eg. $Ca^{2+}$) to the system. Based on this effect, e.g. rFIX can be bound to ion-exchange resins at one specific charge state and eluted from the gel by converting the charge by removing (or adding) $Ca^{2+}$. This principle of separation is called "pseudo affinity chromatography". This principle is reflected also in those vitamin K dependent proteins which do not comprise a Gla-domain. The present inventive method which is applied for the purification of Vitamin K dependent proteins, like e.g. rFIX introduces particular parameter ranges which allow the provision of a superior pharmaceutical preparation of a Vitamin K dependent protein, which is enriched in active Vitamin K dependent protein and preferably essentially free of inactive Vitamin K dependent protein, particularly of inactive full-length Vitamin K dependent protein.

Purification Procedure of rFIX

The inventors developed a recombinant CHO cell line that expresses recombinant human Factor IX based on the CHO DXB11 parenteral cell line. The cell line was engineered in a way that it co-expresses recombinant human Furin to improve the intracellular maturation of pro-FIX to FIX. For the production process, the cells were grown in suspension in chemostat mode and they were adapted to a chemically defined media without any addition of mammalian or plasma derived proteins. Soy peptone was added to the growth media to improve the productivity of the clone.

In a chemostat production campaign the collected cell culture harvest was clarified by depth filtration on Cuno depth filters (with positive zeta potential) and 0.2 pm membrane filtration on PVDF or PES filter membranes to removes cells and cell debris. The filtered cell free harvest represented the starting material for developing the purification process of rFIX.

Various modifications and variations of the described method and products of the invention will be apparent to those skilled in the art without departing from the scope and spirit of the invention. Although the invention has been described in connection with specific preferred embodiments, it should not be unduly limited to such embodiments.

EXAMPLES

Example 1: Determination of Parameter Ranges and Removal of Inactive FIX Objective In this set of experiments, the influence of buffer parameters pH, conductivity and Calcium content on the performance of the Capture step are investigated. The impact on product yield and product quality was evaluated using a statistical design approach.

INTRODUCTION

The rFIX downstream production step "CPN" is a chromatographic purification on an anion exchange column, in this example on Q-Sepharose Fast Flow. The loading material is clarified harvest material from fermentation supplemented with 2 mM EDTA. The large scale purification process applied for the clinical production of rFIX typically starts with a capture step by Anion Exchange chromatography on Q-Sepharose Fast Flow, loading the clarified harvest with a supplementation of 2 mM EDTA and a pH of about 7.0-7.4. The major objective of this capture step is the reduction of process related impurities (media components, production cell derived impurities), removal of product related impurities (truncated rFIX species, rFIX species without calcium sensitivity, FIX-desGLA) and concentration of the product. The critical parameters for the chromatographic Anion Exchange purification step exploiting a calcium effect for a "pseudo" affinity elution were defined by a risk assessment. To further evaluate the rFIX downstream process step, CPN (Capture step), studies at small scale were performed covering the parameters, which were considered critical, i.e. pH (buffers wash 2 and elution buffer), conductivity (buffer wash 2 and elution buffer) and the calcium content (elution buffer) applying a DOE approach. The test material was derived from an rFIX clinical phase III production at Pilot scale. The chromatographic purification runs were analyzed by applying appropriate qualified or validated analytical methods. The resulting data were evaluated, compared to clinical production data and give information about robustness of the step in terms of the current parameter setting. The chromatographic details of the FIX Capture step are described below. The protein load for the sample load was 0.8-1.1 mg FIX antigen per ml resin. The collection started at a significant increase of the $UV_{280}$ slope of more than or equivalent to 0.2 AU (optical pass length: 5 mm) and ends after 4.5 CV. The QFF-Equi buffer was used for equilibration, wash 1 and wash 3, the QFF-wash buffer was used for wash 2. The QFF-elu buffer was used for elution. The 200 mM EDTA stock solution was at pH 7.4±0.1 at room temperature. It had a conductivity of 30-35 mS/cm at 25° C. Planned variations to determine the effect of variations and several parameters were introduced for the wash and elution buffer corresponding to the studied design. The rFIX loading material was taken from clinical phase 3 production campaigns without a freeze/thaw step. The Capture step includes column activation, equilibration, product loading, washings 1, 2, 3 and elution. A column cleaning procedure was used to ensure that no batch to batch carry-over of denatured proteins occurs and prevents column fouling that could impact the column performance.

Experimental Design

Five parameters of the buffers QFF-wash (Wash 2) and QFF-Elu (Elution) were varied including pH, conductivity and the Calcium concentration as shown in Table 1.

TABLE 1

Overview of tested process parameters of the step CPN

| Process variable | Sub variable | Set point or ranges | |
|---|---|---|---|
| | | Specified range | Tested range |
| pH | Wash 2 buffer | 5.9-6.1 | 50-7.0 |
| | Elution buffer | 7.9-8.1 | 7.0-9.0 |
| Conductivity | Wash 2 buffer | 16.5-21.5 | 14/18/22 |
| | Elution buffer | 17.0-22.0 | 14-23 |
| $Ca^{2+}$ concentration | Elution buffer | 2 mM | 1.0-3.0 (+.05 and 6.0) |

In the following Table 2, the actually used process parameters in the Capture step are identified:

| | Process Parameters | | | | | | | | |
|---|---|---|---|---|---|---|---|---|---|
| | Load | | | | Wash 2 | | Elution | | |
| Experiment Name | Load mg/ml | pH | Cond. mS/cm | EDTA mM | pH | Cond. mS/cm | pH | Cond. mS/cm | Ca++ mM |
| Table 2A: Overview of tested process parameters in the step CPN including testing ranges for the DOE experiments | | | | | | | | | |
| F9_04 | 0.90 | 6.97 | 13.41 | 2.0 | 6.03 | 18.48 | 7.92 | 18.23 | 2.0 |
| F9_07 | 0.92 | 7.06 | 13.47 | 2.0 | 6.03 | 18.43 | 7.96 | 19.03 | 2.0 |
| F9_06 | 0.94 | 6.96 | 13.33 | 2.0 | 5.01 | 21.80 | 7.06 | 13.85 | 1.0 |
| F9_09 | 0.80 | 6.97 | 13.46 | 2.0 | 4.97 | 13.99 | 9.09 | 22.60 | 3.0 |
| F9_08 | 0.93 | 6.96 | 13.35 | 2.0 | 5.01 | 21.80 | 9.13 | 22.50 | 1.0 |
| F9_11 | 0.88 | 6.98 | 13.43 | 2.0 | 7.02 | 21.8 | 7.08 | 22.6 | 1.0 |
| F9_10 | 0.80 | 6.99 | 13.28 | 2.0 | 7.04 | 14.27 | 7.02 | 23.00 | 3.0 |
| F9_13 | 0.86 | 6.95 | 13.29 | 2.0 | 5.05 | 13.99 | 9.09 | 13.88 | 1.0 |
| F9_12 | 0.81 | 6.94 | 13.33 | 2.0 | 6.06 | 18.41 | 8.00 | 18.99 | 2.0 |
| F9_15 | 1.07 | 6.95 | 13.41 | 2.0 | 5.05 | 13.93 | 7.00 | 13.90 | 3.0 |
| F9_14 | 0.97 | 6.92 | 13.35 | 2.0 | 5.03 | 13.92 | 7.06 | 22.70 | 1.0 |
| F9_17 | 0.96 | 6.94 | 13.21 | 2.0 | 5.04 | 21.81 | 9.07 | 13.86 | 3.0 |
| F9_16 | 0.83 | 6.92 | 13.26 | 2.0 | 7.03 | 21.90 | 7.05 | 13.92 | 3.0 |
| F9_18 | 0.88 | 7.01 | 13.48 | 2.0 | 7.00 | 22.00 | 9.11 | 13.92 | 1.0 |
| F9_20 | 0.88 | 6.97 | 13.78 | 2.0 | 7.04 | 14.21 | 9.09 | 22.90 | 1.0 |
| F9_19 | 0.83 | 7.00 | 13.34 | 2.0 | 5.02 | 21.90 | 7.06 | 22.90 | 3.0 |
| F9_22 | 0.82 | 6.96 | 13.55 | 2.0 | 7.04 | 14.21 | 9.10 | 13.86 | 3.0 |
| F9_21 | 0.85 | 6.97 | 13.87 | 2.0 | 7.02 | 14.14 | 7.02 | 13.97 | 1.0 |
| F9_27 | 0.75 | 6.99 | 12.93 | 2.0 | 7.01 | 22.20 | 9.09 | 22.60 | 3.0 |
| Table 2B: Overview of tested process parameters of the step CPN including testing ranges for the DOE experiments | | | | | | | | | |
| F9_23 | 0.83 | 6.97 | 13.45 | 2.0 | 6.04 | 18.57 | 8.02 | 19.20 | 2.0 |
| F9_28 | 0.88 | 6.99 | 12.83 | 2.0 | 6.06 | 18.69 | 8.11 | 19.23 | 1.0 |
| F9_29 | 0.79 | 6.99 | 13.17 | 2.0 | 6.06 | 18.69 | 8.12 | 19.24 | 3.0 |
| F9_30 | 0.95 | 6.96 | 13.32 | 2.0 | 5.03 | 18.51 | 7.99 | 19.23 | 2.0 |
| F9_31 | 0.97 | 6.97 | 13.32 | 2.0 | 5.97 | 22 | 7.97 | 19.23 | 2.0 |
| F9_32 | 1.05 | 6.98 | 13.54 | 2.0 | 7.00 | 19.02 | 7.99 | 19.23 | 2.0 |
| F9_33 | 0.83 | 6.99 | 13.57 | 2.0 | 6.06 | 14.01 | 7.97 | 19.23 | 2.0 |
| F9_34 | 0.83 | 6.99 | 13.05 | 2.0 | 6.05 | 18.67 | 6.96 | 19.70 | 2.0 |
| F9_35 | 0.82 | 7.02 | 13.45 | 2.0 | 6.04 | 18.44 | 8.06 | 14.02 | 2.0 |
| F9_36 | 0.76 | 6.97 | 13.20 | 2.0 | 6.05 | 18.67 | 9.13 | 18.42 | 2.0 |
| F9_37 | 0.84 | 6.98 | 13.4 | 2.0 | 6.05 | 18.49 | 8.09 | 22.9 | 2.0 |
| F9_38 | 0.98 | 7.00 | 12.68 | 2.0 | 6.05 | 18.67 | 8.05 | 18.85 | 0.5 |
| F9_39 | 0.83 | 6.97 | 13.45 | 2.0 | 6.00 | 18.49 | 7.96 | 19.35 | 2.0 |
| F9_40 | 0.79 | 6.98 | 13.26 | 2.0 | 5.98 | 18.56 | 8.03 | 19.85 | 6.0 |
| F9_41 | 0.82 | 7.00 | 13.17 | 2.0 | 5.98 | 18.56 | 7.92 | 19.12 | 2.0 |

A fine tuning became possible only after the research as conducted by the present inventors who surprisingly found that the 1-3 mM Calcium range is particularly suitable and needs to be combined with very particularly chosen ranges of conductivity and pH.

Example 2: Further Investigation of rFIX Degradation Products

Methods

FIX potency was determined with a one step clotting procedure using FIX depleted plasma.

FIX potency was determined with a chromogenic assay that measures the activity of formed with a kinetic evaluation method. FIX is converted to FIXa by FXIa and Thrombin contained in the kit.

FIX antigen was analyzed with a sandwich ELISA using polyclonal affinity purified antibodies for coating and detection.

FIXa was determined with a chromogenic assay that generates FXa in the presence of phospholipids, calcium and activated FVIII. FXa cleaves the chromogenic peptide substrate and releases pNA that is measured at 405 nm.

SDS-PAGE was performed using 12% gels under reducing conditions. Western Blot analysis of separated polypeptides was done with polyclonal anti FIX IgGs as primary antibodies.

Densitometry:

The fresh developed Western Blot was digitalized using the Image Scanner III (GE Healthcare) and the Software Labscan 6.0. The densitometry was performed with the Software package Image Quant TL (GE Healthcare). Along a vertical axis the band intensity and width is determined and the area under the curve correlates with the antigen amount of the bands. The sum of all bands was fixed as 100%, the individual bands are expressed in percentage of total amount.

Results

Removal of an inactive full length rFIX species at the Capture Anion Exchange purification step became possible by working in specific parameter ranges (data not shown). The results are reflected by the DOE calculation, which is shown in FIGS. 1-2. It becomes evident that the inventors have been successful in identifying parameter ranges for a concentration of 1-3 mM calcium for both conductivity and pH in the elution step of the ("first") anion exchange chromatography. When working within these ranges, the parameters can be adapted to the need of the process in question, as long as the elution is worked in the hatched area as shown in these figures. These areas are also defined as preferred embodiments in the general part of this invention above.

Thus, the present invention provides advantageous parameter ranges as a contribution to the art for the provision of a FIX preparation which is essentially free of inactive, full length FIX, The capture purification is performed on a Q-Sepharose Fast Flow resin applying a high salt wash at low pH and a calcium induced product elution at high pH. The purification procedure as applied for the rFIX clinical production is outlined in Table 3, the buffer formulations are summarized in Table 4.

TABLE 3

Final purification schema for FIX Capture on Q Sepharose Fast Flow

| Step | | Buffer | Amount CV | Flow rate cm/h |
|---|---|---|---|---|
| 1 | Resin activation | QFF-activation | ≥2.0 | 150 |
| 2 | equilibration | QFF-Equi | ≥4.0 | 150 |
| 3 | Sample Load | Cell free CCS supplemented with 2 mM EDTA | Appr. 125 CV | 150 |
| 3.1 | Loading range | | Protein load: 0.4-2.0 mg FIX Ag/ml resin | |
| 4 | Wash 1 | QFF-Equi | ≥2.0 | 150 |
| 5 | Wash 2 | QFF-Wash | ≥5.0 | 100 |
| 6 | Wash 3 | QFF-Equi | ≥2.0 | 100 |
| 7 | elution | QFF elu | ≥5.0 | 50 |
| 7.1 | Pool collecting | | Collecting starts as significant increase of $UV_{280}$ slope ≥0.2 AUs (optical path length: 5 mm) and ends after 4.5 CV | |

The chromatographic purifications were performed at 2-8° C. at lab scale, the specification for the clinical phase III production is 2-15°

TABLE 4

Composition of buffers for the Q-Sepharose Capture step

| Buffer ID Buffer | Steps | Composition | Conductivity [mS/cm] at 25° C. |
|---|---|---|---|
| QFF-act | Resin activation | 2000 mM NaCl | ~160 |
| QFF-Equi | Equilibration, Wash 1, wash 3 | 20 mM Tris, 2 mM EDTA, pH = 7.4 ± 0.1 at RT | 1.5-2.5 |
| QFF-wash | Wash 2 | 20 mM MES, 180 mM NaCl, 2 mM EDTA, pH = 6.0 ± 0.1 at RT | 16.5-21.5 |
| QFF-Elu | Elution | 20 mM Tris, 180 mM NaCl, 2 mM $CaCl_2$, pH = 8.0 ± 0.1 at RT | 17-22 |
| EDTA stock | EDTA supplementation of load | 200 mM EDTA, pH = 7.4 ± 0.1 at RT | 30-35 |

Samples were analyzed by SDS-PAGE and anti-FIX Western Blotting. It can be seen in SDS-PAGE (results not shown) that a significant amount of impurities (CHO HCP and truncated FIX proteins) is removed during loading wash 2 or remain on the column and are eluted in the high salt cleaning step. The product elutes with high purity and homogeneity during the Calcium induced elution at pH=8.0. The position of the major truncated form is present primarily in wash 2.

Flow Through Fraction

In this fraction, a major truncated FIX species with approximate molecular mass of 60 kDa and traces of rFIX species with a molecular weight of 51 kDa can be found. The full length FIX shows an apparent molecular mass of about 75 kDa in this gel system. The amount of truncated rFIX polypeptides in this fraction is very low and no clotting or chromogenic activity could be measured (data not shown). About 1-1.5% of the total antigen loaded can be found in this wash fraction according to the Antigen ELISA data, densitometric analyses indicate that about 0.4-0.5% of the total protein loaded are truncated FIX species found in this fraction.

Wash 2 Fraction

In this fraction, a truncated FIX species with approximate molecular mass of 60 kDa is washed off the column. The full length FIX shows an apparent molecular mass of about 75 kDa in this gel system. The truncated rFIX polypeptide has no clotting or chromogenic activity. N-terminal sequencing results indicated that the truncation must be at the C-terminus and that the N-terminal GLA domains are incomplete. About 6-8% of the total antigen loaded can be found in this wash fraction according to the Antigen ELISA data, densitometric analyses indicate that about 15-16% of the total protein loaded are truncated FIX species found in this fraction.

As the amount of truncated FIX species is not increasing when comparing the filtered harvest with the chromatographic fractions of the CPN capture step, the truncation of rFIX most probably happens during fermentation within the cell or in the cell culture supernatant by yet unidentified cellular proteases. The downstream step CPN does not contribute to or increase the content of this truncated rFIX species.

Eluate Pool Fraction

The results of the SDS-PAGE indicate that in the eluate pool a full length FIX species is enriched and only traces of truncated FIX species can be detected. The FIX specific activities show that the specific activities are significantly higher in the eluate pool. The increase in specific activity in the eluate pool correlates with the fact that significant amounts of inactive FIX species are removed at this purification step during wash 2 and the high salt column cleaning step. About 61-72% of the FIX antigen detected in the filtered harvest (=load) by the ELISA method are found in the eluate pool of the Capture purification step CPN. The densitometric analyses indicate that about 68-75% of the total FIX loaded onto the CPN step are found as full length rFIX in the eluate pools which correlates with the FIX ELISA data (data not shown).

High Salt Cleaning Fraction (Post Eluate).

In the column high salt cleaning fraction a significant amount of inactive full length FIX can be detected. About 23-28% of the total FIX antigen loaded can be found in this column cleaning fraction according to the antigen ELISA data, densitometric analyses indicate that about 22-30% of the total FIX antigen loaded are found as full length inactive FIX in this fraction.

Robustness of Removal of Inactive FIX Species at the Step CPN

During small scale robustness studies relevant process parameters for the elution conditions have been investigated.

For the elution buffer the parameters conductivity, pH and Calcium concentration were investigated in a small scale DOE study. Under elution conditions of 6 mM Calcium part of the inactive FIX antigen seems to co-elute with the product and the FIX antigen in the high salt cleaning fraction is reduced to 5.9%. Under conditions of a high conductivity of the elution buffer also part of the inactive FIX antigen seems to co-elute with the product and the FIX antigen in the high salt cleaning fraction is reduced to 16.4%. In both cases the FIX product pool would be contaminated with a certain percentage of full length inactive FIX.

Further experiments have also been conducted, wherein, FVII has been used as target protein. Upon working in the described parameter ranges, the removal of inactive protein could be confirmed (data not shown).

The invention claimed is:

1. A method for the purification of an active Vitamin K-dependent protein comprising the steps of:
    (a) loading a first anion exchange resin material with the Vitamin K-dependent protein in a loading buffer in the absence or low concentration of divalent cations;
    (b) performing at least three washing steps with washing buffers that are absent of said divalent cations but that contain counter anions, wherein the first washing buffer has a pH between 6.8 and 7.5, the second washing buffer has a pH between 5.5 and 6.5, and the third washing buffer has a pH between 7.0 and 8.2,
    (c) eluting the Vitamin K-dependent protein with an eluant comprising 1-3 mM calcium and a counter-anion to form an eluate containing the active Vitamin K dependent protein, wherein
        the eluant has a conductivity between 15 and 22 mS/cm (25° C.), and
        a pH of between 7.0 and 9.0;
    (d) diluting the obtained eluate pool, and increasing the concentration of the calcium,
    (e) loading a second anion exchange resin material with the diluted eluate pool as obtained after step (c); and
    (f) collecting the flow-through containing the active Vitamin K-dependent protein.

2. The method according claim 1, wherein the first and second anion exchange resin materials each have a positively charged group which is independently selected from the group, consisting of diethylaminoethane (DEAE), dimethylaminoethane (DMAE), trimethylaminoethyl (TMAE), polyethyleneimine (PEI), quaternary aminoalkyl, quaternary aminoethane (QAE), and quaternary ammonium (Q).

3. The method according to claim 1, wherein the active Vitamin K-dependent protein is selected from the group consisting of Factor II, Factor VII, Factor IX, Factor X, Protein C, and Protein S.

4. The method according to claim 1, wherein the elution buffer in step (b) further comprises 180 mM NaCl.

5. The method according to claim 1, wherein step (c) includes diluting the obtained eluate pool to lower the conductivity.

6. The method according to claim 3, wherein the active Vitamin K-dependent protein is Factor IX.

7. The method according to claim 1, wherein in step (c) the eluant comprises 2 mM calcium and the counter-anion.

8. The method according to claim 1, wherein in step (c) the eluant has a conductivity between 16.9 to 22 mS/cm (25° C.).

9. The method according to claim 1, wherein in step (b) the second washing buffer has a pH between 5.9 and 6.1.

* * * * *

UNITED STATES PATENT AND TRADEMARK OFFICE
CERTIFICATE OF CORRECTION

PATENT NO.         : 10,202,417 B2  
APPLICATION NO.    : 14/776622  
DATED              : February 12, 2019  
INVENTOR(S)        : Artur Mitterer et al.

Page 1 of 1

It is certified that error appears in the above-identified patent and that said Letters Patent is hereby corrected as shown below:

On the Title Page

Under the assignees' names, "Bazalta GmbH" should be changed to --Baxalta GmbH--.

Signed and Sealed this
Twenty-fifth Day of February, 2020

Andrei Iancu
*Director of the United States Patent and Trademark Office*